US005757002A

United States Patent [19]
Yamasaki et al.

[11] Patent Number: 5,757,002
[45] Date of Patent: May 26, 1998

[54] METHOD OF AND APPARATUS FOR MEASURING LACTIC ACID IN ORGANISM

[75] Inventors: Yutaka Yamasaki; Hisashi Okuda; Koji Matsuoka; Kexin Xu, all of Kyoto, Japan

[73] Assignee: Kyoto Dai-Ichi Kagaku Co., Ltd., Kyoto, Japan

[21] Appl. No.: 704,987

[22] Filed: Aug. 29, 1996

[30] Foreign Application Priority Data

Aug. 30, 1995 [JP] Japan ................................ 7-246851

[51] Int. Cl.$^6$ ................................................ A61B 5/00
[52] U.S. Cl. ............................. 250/339.12; 128/633
[58] Field of Search ........................ 250/339.12, 349.09, 250/341.2, 341.8; 128/633, 664

[56] References Cited

U.S. PATENT DOCUMENTS

| | | |
|---|---|---|
| 4,281,645 | 8/1981 | Jöbsis . |
| 4,505,583 | 3/1985 | Konomi ................................. 356/73 |
| 4,805,623 | 2/1989 | Jobsis ................................. 250/339.12 |
| 5,361,758 | 11/1994 | Hall et al. . |
| 5,379,764 | 1/1995 | Barnes et al. ........................ 250/339.12 |
| 5,433,197 | 7/1995 | Stark ................................... 128/633 |
| 5,435,309 | 7/1995 | Thomas et al. ..................... 128/633 |
| 5,441,054 | 8/1995 | Tsuchiya ............................. 128/665 |
| 5,459,317 | 10/1995 | Small et al. ......................... 250/341.8 |

FOREIGN PATENT DOCUMENTS

| | | |
|---|---|---|
| 0 419 223 | 3/1991 | European Pat. Off. . |
| 0 548 418 | 6/1993 | European Pat. Off. . |
| 0 589 191 | 3/1994 | European Pat. Off. . |
| 6-245938 | 9/1994 | Japan . |
| 92 00513 | 1/1992 | WIPO . |
| 95 22046 | 8/1995 | WIPO . |

OTHER PUBLICATIONS

Proceedings of the Annual Northeast Bioengineering Conference, Kingston, Rhode Island, Mar. 12–13, 1992, No. Conf. 18, Mar. 12, 1992, Ohley W J, pp. 105/106; Stohr E. et al: Quantitative FTIR Spectrophometry of Cholesterol and Other Blood Constituents and Their Interference With the In–Vitro Measurement of Blood Glucose.

Applied Optics, vol. 35, No. 1, Jan. 1, 1996, pp. 209–212; Berger A. J. et al: Rapid, Noninvasive Concentration Measurements of Aqueous Biological Analytest by Near–Infrared Raman Spectroscopy.

*Primary Examiner*—David P. Porta
*Assistant Examiner*—Richard Hanig
*Attorney, Agent, or Firm*—Nikaido, Marmelstein, Murray & Oram LLP

[57] ABSTRACT

A light source pa light of a plurality of wavelengths of a near infrared region, and a spectroscopic part selects a wavelength subjected to absorption by lactic acid as a measuring wavelength from measuring light of a plurality of wavelengths emitted from the light source part. A probe comes into contact with an organism measuring portion and irradiates the organism measuring portion with the measuring light of the wavelength selected by the spectroscopic part, while a photoreceiving part detects transmitted/scattered light of the measuring light incident upon the organism measuring portion. A light signal detected by the photoreceiving part is converted to absorbance in a signal processing part, so that the concentration of lactic acid is calculated by a host computer serving as an arithmetic-control part and displayed on a display part. No reagent is required, while difference between lactic acid concentrations varied with measuring portions can also be noninvasively measured.

17 Claims, 9 Drawing Sheets

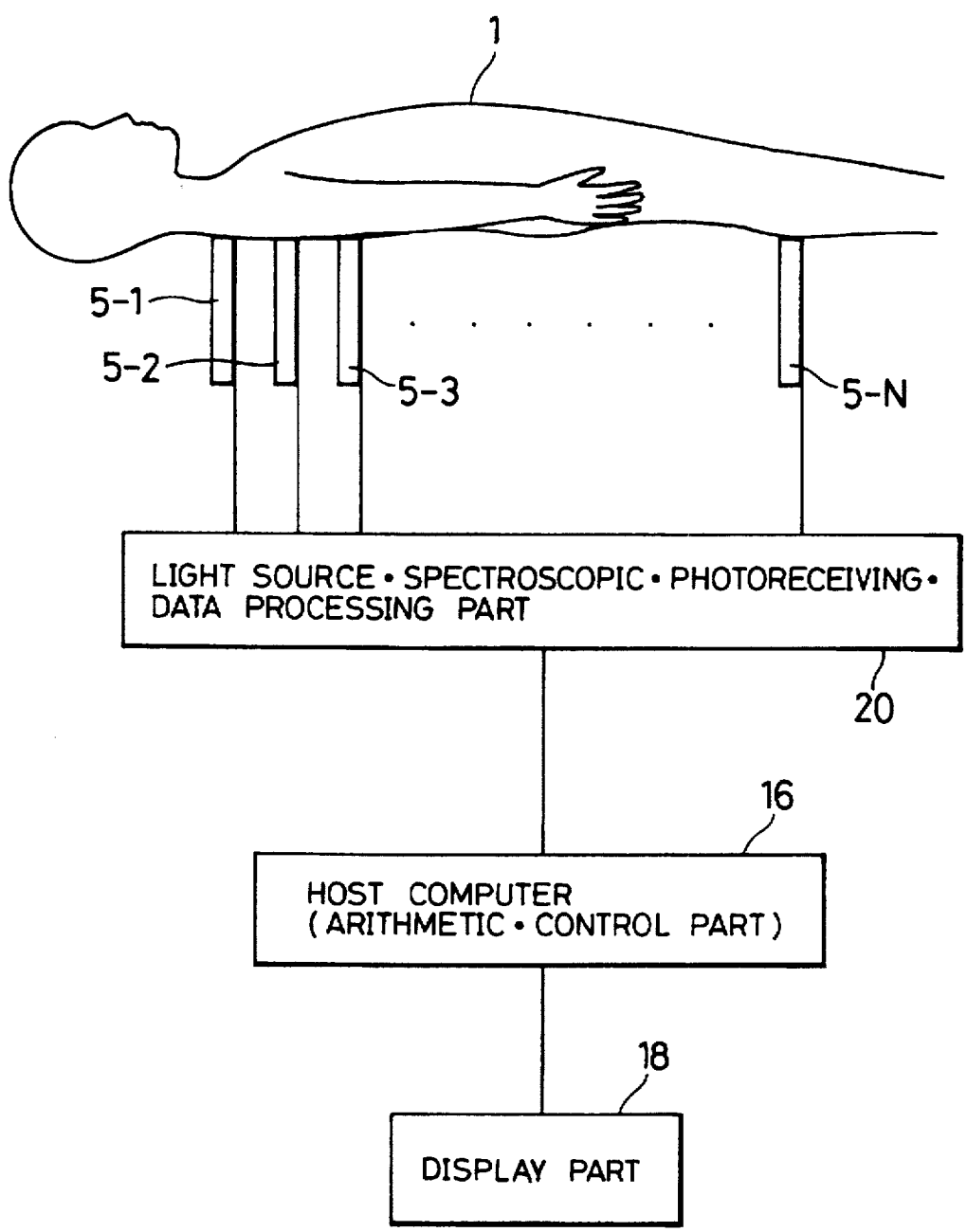

Fig. 9B     Fig. 9A
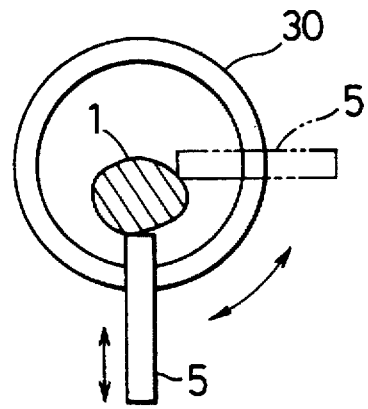
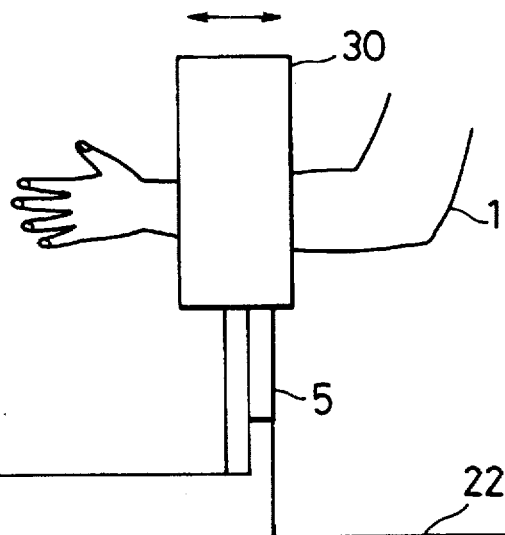
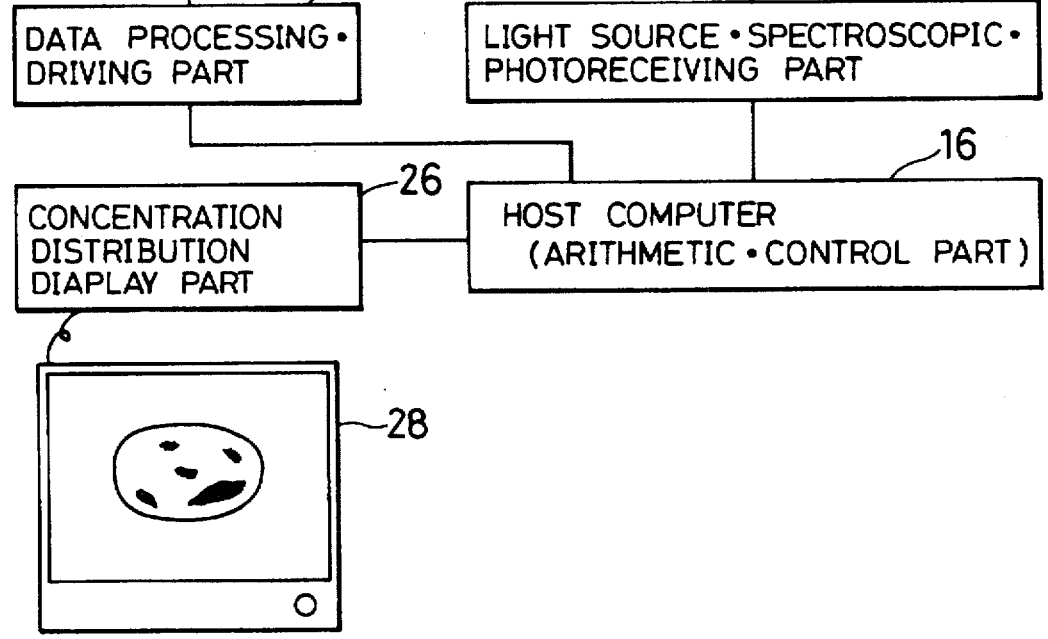

METHOD OF AND APPARATUS FOR MEASURING LACTIC ACID IN ORGANISM

BACKGROUND OF THE INVENTION

1. Field of the Invention

The present invention relates to a method of and an apparatus for measuring lactic acid in organism in the field of sports medicine or exercise physiology.

2. Description of the Background Art

It is known that lactic acid accumulates by intramuscular glycolysis as a result of exercise. The amount of the accumulating lactic acid is highly correlated with the degree of fatigue, and hence the intravascular concentration of lactic acid which is carried from muscles into the blood is measured as a management index for training in the field of sports medicine or exercise physiology.

A method of measuring a urogenous lactic acid concentration has been proposed as a method of noninvasively measuring the lactic acid concentration (refer to Japanese Patent Laying-Open Gazette No. 5-3798 (1993).

In each of methods of measuring intravascular lactic acid and urogenous lactic acid, an enzyme such as lactate oxidase or lactate dehydrogenase is employed as a reagent.

In a measuring method which is directed to the blood, it is necessary to collect the blood, leading to pain in blood collection or a possibility of infection. Further, both of the methods of measuring intravascular lactic acid and urogenous lactic acid require reagents, leading to complicated operations and high costs.

While the intramuscular lactic acid concentration heterogeneously distributes, local difference of the intramuscular lactic acid concentration cannot be measured by intravascular or urogenous lactic acid measurement.

SUMMARY OF THE INVENTION

An object of the present invention is to provide a method of measuring intravital lactic acid capable of noninvasively measuring difference between lactic acid concentrations which are varied with measured portions with no requirement for a reagent, and an apparatus employed for the method.

According to the present invention, an organism is irradiated with near infrared light, so that the intravital lactic acid concentration is quantitatively analyzed through light which is transmitted/scattered through/from the organism.

The term "transmitted/scattered" means such a phenomenon that light enters a light scattering target substance and goes out from the target substance, and a term "transmitted/ scattered light" includes both of the so-called transmitted light going out in the direction of incidence of the light and the so-called reflected light going out in a direction opposite to the direction of incidence.

According to an aspect of the present invention, a light intensity at a measuring wavelength is detected from light transmitted/scattered through/from an organism on the assumption that a wavelength which is subjected to absorption by lactic acid in a near infrared region is the measuring wavelength, so that the intravital lactic acid concentration is quantitatively analyzed on the basis of the light intensity.

In order to guide a calibration expression for obtaining a lactic acid concentration from an obtained absorption spectrum, it is necessary to remove interference by another component of an organism measuring portion. As one of such methods, there is a method employing multivariate analysis. In a multivariate analytical operation, multivariate regression analysis such as principal component regression analysis (PCR) or partial least square fitting (PLS) is employed for performing data analysis. Regression analysis can be made by employing a number of spectral intensities at once in the multivariate regression analysis, whereby quantitative analysis in higher accuracy is possible as compared with single regression analysis. While multiple regression analysis is most generally employed, a number of samples are necessary and its quantitative analytical accuracy is reduced if correlation between spectral intensities at respective wavenumbers is high. On the other hand, PCR which is multivariate regression analysis can intensify spectral intensities in a plurality of wavenumber regions to principal components which are irrelevant to each other while deleting unnecessary noise data, whereby high quantitative analytical accuracy can be attained. Further, PLS can also utilize sample concentration data in case of extracting a principal component, whereby high quantitative analytical accuracy can be attained similarly to PCR. As to the multivariate regression analysis, Tahenryo Kaiseki (by Kazuo Nakatani, Shinyo-Sha, Japan) can be referred to.

In order to extract necessary information from a spectrum complicatedly fluctuating by various fluctuation factors, data processing by a computer is remarkably useful. A typical processing method is stored in processing software which is provided on a commercially available near infrared apparatus or the like. An example of such commercially available software is "Unscramber" by CAMO Company. Typical processing methods are the aforementioned multiple regression analysis, PLS, the principal component regression analysis and the like.

Large flows of data processing which is applied to quantitative analysis are (1) formation of a calibration model, (2) evaluation of the calibration model, and (3) determination of an unknown sample.

In order to perform calibration, it is necessary to measure a proper number of samples for forming a calibration curve in sufficient accuracy. Obtained spectra are pretreated at need. Typical pretreatments are smoothing of spectra, differential and normalization, which are general processing methods.

The calibration is processing of constructing a numerical relational expression between spectral data and an analytical value of a target characteristic, i.e., a model. The model is formed by a statistical technique with analytical values of the samples for forming a calibration curve and the spectral data.

In order to correctly evaluate accuracy of prediction of the formed calibration curve with respect to an unknown sample, a measurement error with respect to the unknown sample is obtained through an evaluation sample. If a determination is made that the accuracy of the calibration curve is insufficient, the type of the processing method or parameters are changed at need, for correcting the calibration curve.

A calibration curve which is regarded as having sufficient accuracy is employed as a relational expression for predicting the value of the target characteristic from the spectral data in analysis of the unknown sample, for determining the unknown sample concentration.

In case of applying multivariate analysis to the inventive method, light intensities at measuring wavelengths are detected respectively from light transmitted/scattered through/from an organism on the assumption that a plurality of wavelengths subjected to absorption by lactic acid in a near infrared region are the measuring wavelengths, so that the intravital lactic acid concentration is quantitatively analyzed from the light intensities through multivariate analysis.

The measuring wavelengths are wavelengths whose correlation coefficients R between lactic acid concentrations and absorbance values are at least 0.8, preferably at least 0.9, in aqueous lactic acid solution measurement. Each correlation coefficient R is calculated as follows:

$$R = \frac{\sum_{i=1}^{n}\{(xi-X)(yi-Y)\}}{\sqrt{\left[\sum_{i=1}^{n}(xi-X)^2\right]\left[\sum_{i=1}^{n}(yi-Y)^2\right]}}$$

where xi represents the concentration of each component at each point, yi represents absorbance with respect to xi, X represents the mean value of the concentration of each component, and Y represents the mean value of the absorbance.

The measuring wavelengths for lactic acid can be selected from near infrared regions expressed in wavenumbers of 6300 to 5400 $cm^{-1}$ and 4800 to 4200 $cm^{-1}$.

A measuring apparatus according to the present invention for measuring lactic acid in organism comprises a light source part for emitting light of a plurality of wavelengths in a near infrared region, a probe which comes into contact with an organism measuring portion for irradiating the organism measuring portion with the light from the light source part as measuring light, a photoreceiving part for detecting transmitted/scattered light of the measuring light received from the organism measuring portion, a spectroscopic part which is provided on an optical path for irradiating the organism measuring portion with the measuring light or that for introducing the transmitted/scattered light of the measuring light into the photoreceiving part for selecting one or a plurality of wavelengths subjected to absorption by lactic acid and selected as a measuring wavelength or measuring wavelengths for lactic acid from the measuring light of the plurality of wavelengths emitted from the light source part, and an arithmetic part for calculating the lactic acid concentration on the basis of a light intensity or light intensities at the measuring wavelength(s) detected by the photoreceiving part.

It is also possible to use a laser unit, a laser diode or a light emitting diode which emits wavelength light of a near infrared region selected as the measuring wavelength(s) as the light source part, and no spectroscopic part is necessary in this case.

In order to perform absorbance measurement at a plurality of wavelengths with employment of no spectroscopic part, measuring light of a plurality of wavelengths can be successively generated by providing a plurality of types of laser diodes or light emitting diodes having different emission wavelengths as a light source and successively switching and turning on the same.

Intravital lactic acid is localized in muscles.

Therefore, it is preferable that local distribution of the intravital lactic acid can be measured. In order to satisfy such a requirement, a plurality of probes are arranged on different measuring portions of an organism respectively for simultaneously irradiating the plurality of measuring portions with the measuring light according to another aspect of the present invention, while the photoreceiving part consists of a plurality of multichannel photoreceiving parts which are arranged on positions corresponding to the respective probes for simultaneously detecting transmitted/scattered light of the measuring light applied from the respective probes, and the apparatus further comprises a display part for imaging and displaying the lactic acid concentrations at the measuring portions calculated by the arithmetic part in response to the measuring portions.

According to still another aspect of the present invention, a set of a probe and a photoreceiving part corresponding thereto are provided and the probe and the photoreceiving part are so supported that the same can scan different measuring portions of an organism while keeping mutual positional relation therebetween, and the apparatus further comprises a memory device for storing the lactic acid concentration of each measuring portion calculated by the arithmetic part, and a display part for imaging and displaying lactic acid concentration distribution on the basis of the data stored in the memory device.

According to a further aspect of the present invention a single probe and a plurality of photoreceiving parts are arranged on a circumference enclosing an organism, the photoreceiving parts are multichannel photoreceiving parts simultaneously detecting transmitted/scattered light of measuring light which is applied from the probe, the probe and the photoreceiving parts are supported to rotatively move along the circumference, and the apparatus further comprises an image processor for forming a tomographic image by the lactic acid concentration of the organism on the basis of lactic acid data of respective measuring portions calculated by the arithmetic part on the basis of light signals detected by the respective photoreceiving parts and a display part for displaying the tomographic image.

According to the inventive method, no reagent is required, and difference between lactic acid concentrations which are varied with the measuring portions can also be noninvasively measured. Consequently, it is possible to recognize the degree of fatigue at every portion of the organism.

It is possible to readily measure difference between lactic acid concentrations which are varied with the measuring portions by making measurement on a plurality of places of the organism at the same time or by making scanning.

The foregoing and other objects, features, aspects and advantages of the present invention will become more apparent from the following detailed description of the resent invention when taken in conjunction with the accompanying drawings.

BRIEF DESCRIPTION OF THE DRAWINGS

FIG. 8 is a block diagram schematically showing an embodiment of an apparatus for measuring lactic acid concentration distribution;

FIG. 9A is a block diagram schematically showing an embodiment of an apparatus for measuring a tomographic image of an organism by lactic acid concentration distribution; and FIG. 9B is a sectional view showing a portion around a probe of the measuring apparatus shown in FIG. 9A and an organism.

DESCRIPTION OF THE PREFERRED EMBODIMENTS

Figure 1:
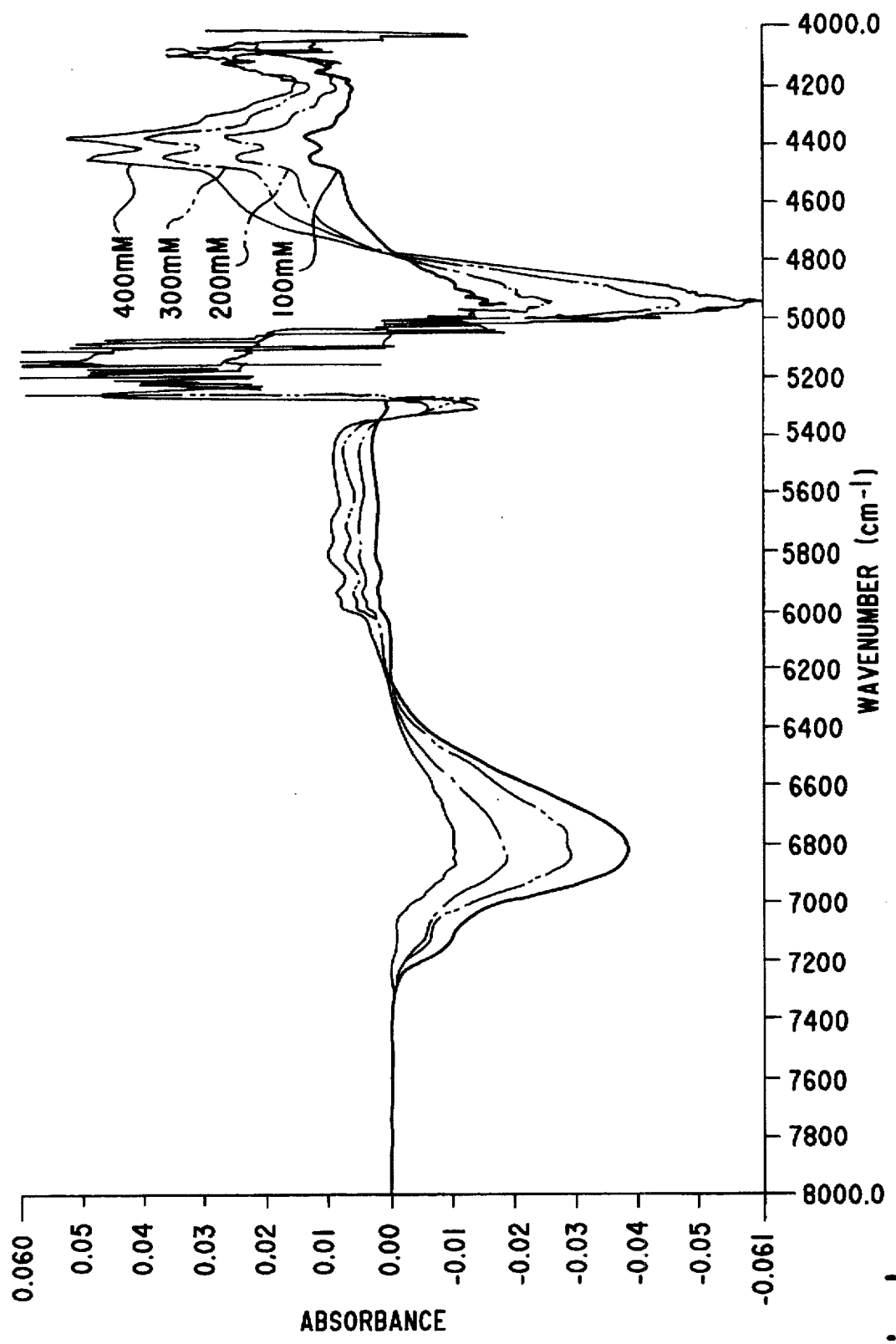
FIG. 1 illustrates absorption spectra of aqueous lactic acid solutions in a near infrared region.

FIG. 1 illustrates absorption spectra of aqueous lactic acid solutions in a near infrared region. The samples are four types of aqueous solutions having concentrations of 100 mM, 200 mM, 300 mM and 400 mM respectively. Bands changing absorbance values in proportion to the concentrations are recognized everywhere, to characterize the lactic acid absorption spectra. These bands are expressed in wavenumbers as 6300 to 5400 $cm^{-1}$ and 4800 to 4200 $cm^{-1}$.

Figure 2:
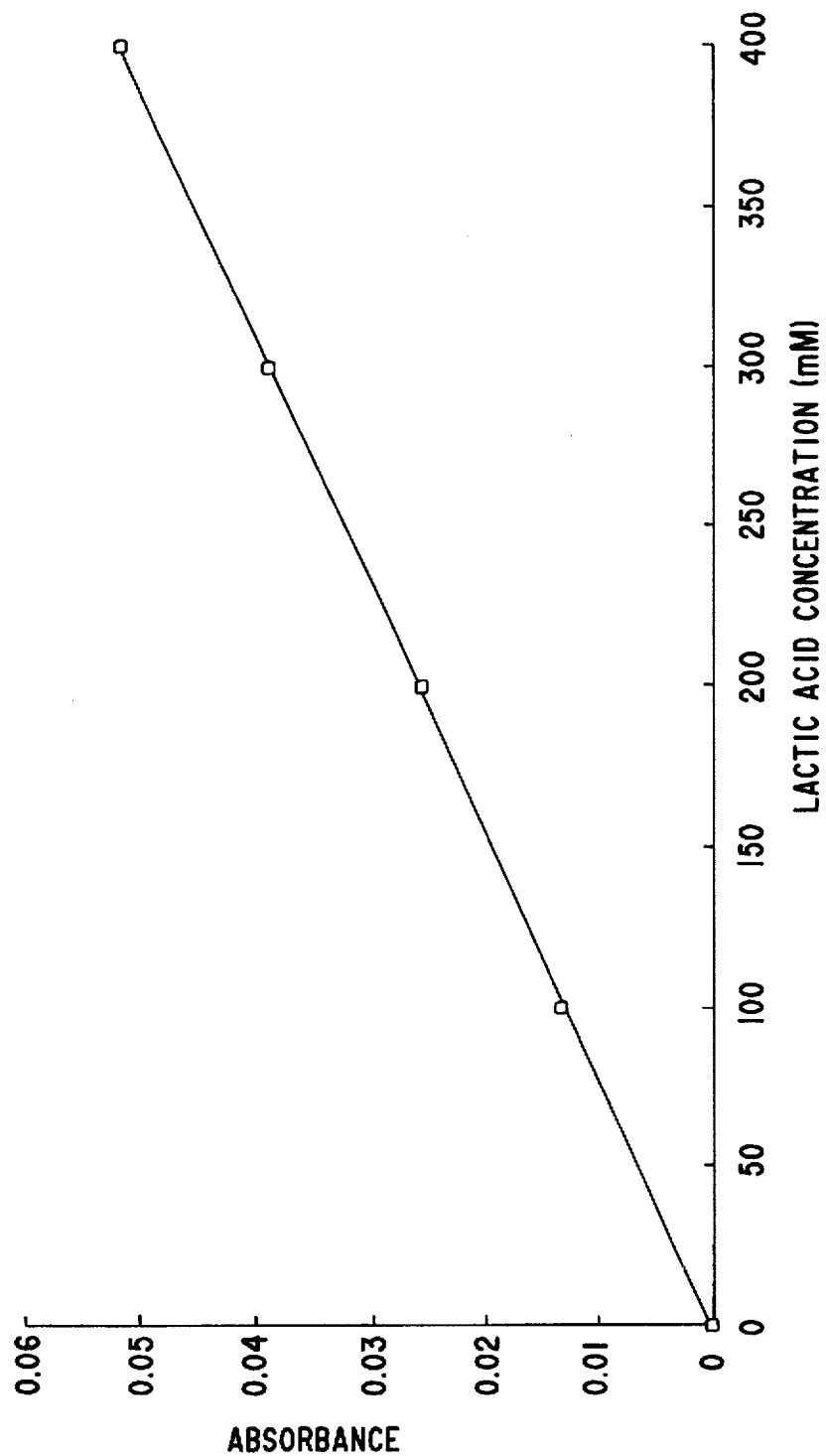
FIG. 2 illustrates a calibration curve obtained by plotting absorbance values of aqueous lactic acid solutions at an absorption wavenumber of 4361.5 $cm^{-1}$ with respect to concentrations.

A calibration curve obtained by plotting the absorbance values at the characteristic absorption wavenumber of 4361.5 $cm^{-1}$ with respect to the concentrations is that shown in FIG. 2. The linearity of the calibration curve shown in FIG. 2 is 0.999967 when expressed in a correlation coefficient R, and this indicates that the same is excellent as a calibration curve. Such a calibration curve can be formed in a wavenumber region having a correlation coefficient of at least 0.8, preferably at least 0.9.

Figure 3:
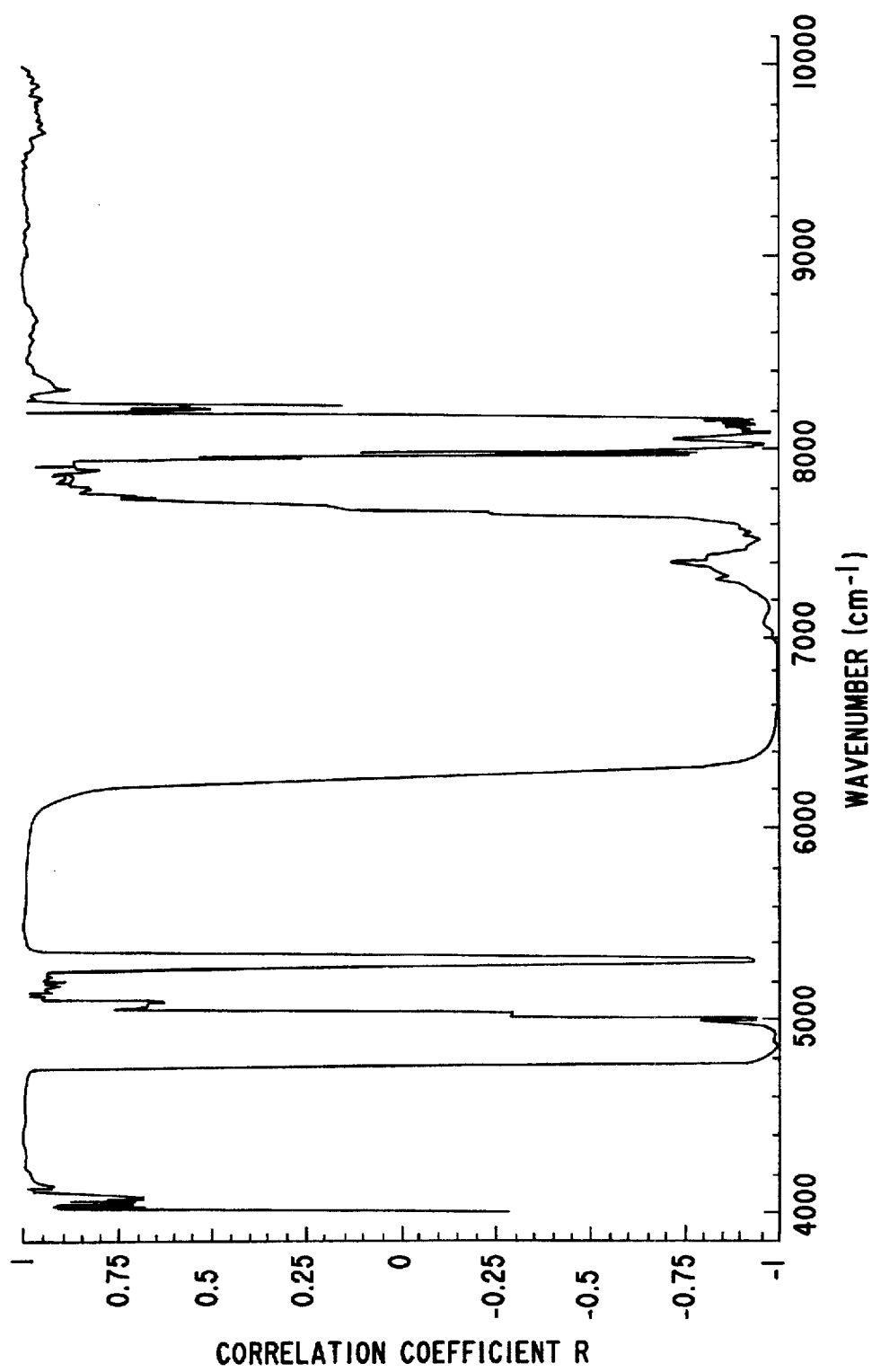
FIG. 3 illustrates results obtained by calculating correlation coefficients R of the absorbance values and the concentrations from the absorption spectra of FIG. 1 as to respective wavenumbers.

FIG. 3 illustrates results obtained by calculating correlation coefficients R of the absorbance values and the concentrations from the absorption spectra of FIG. 1 as to the respective wavenumbers. High correlation coefficients are obtained in a number of wavenumber bands, and a high accuracy calibration expression of lactic acid is obtained when a multivariate analytical operation such as PCR or PLS is performed in the wavenumber regions having high correlation coefficients.

Figure 4:
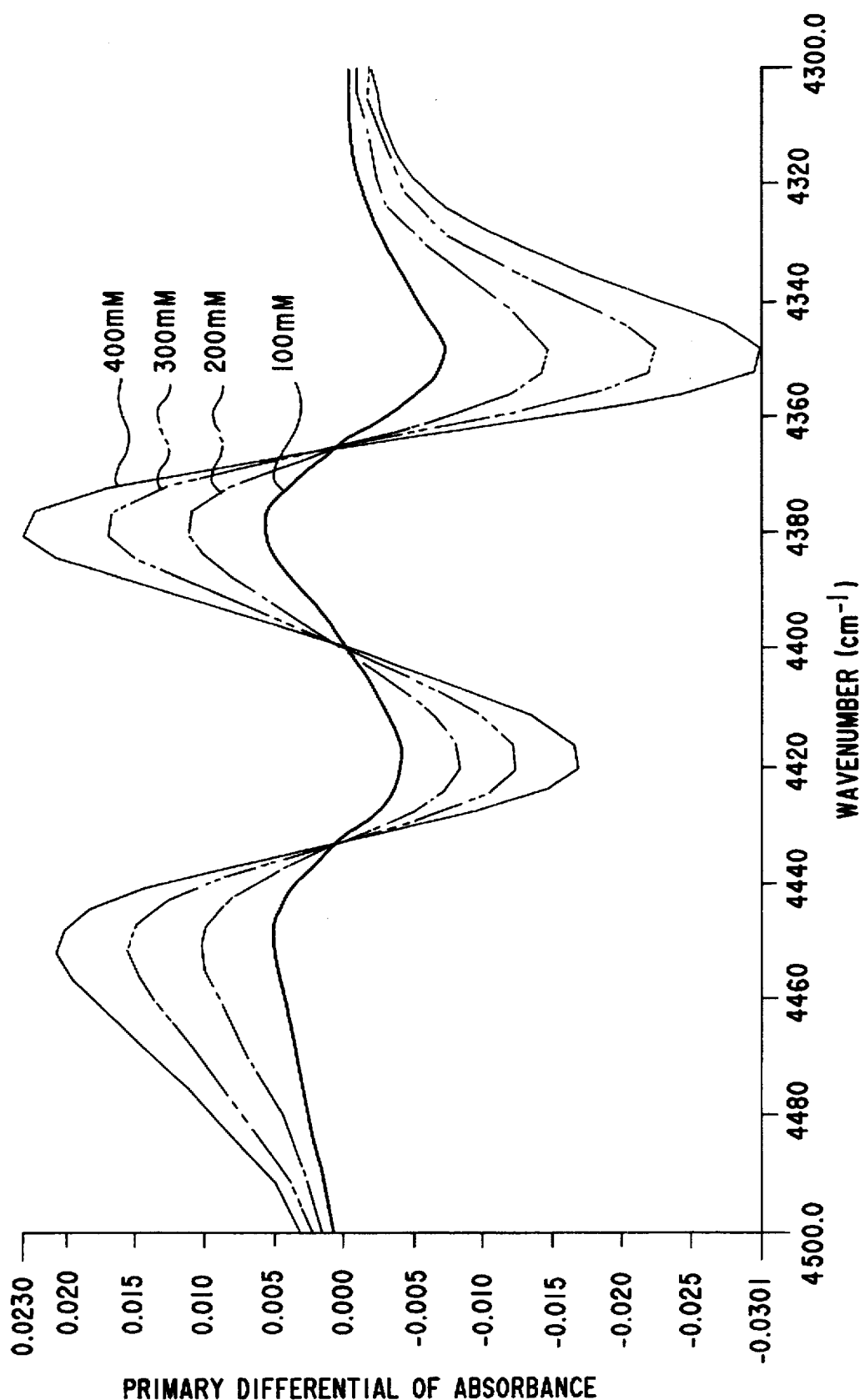
FIG. 4 illustrates results obtained by primarily differentiating parts of the absorption spectra shown in FIG. 1.
Figure 5:
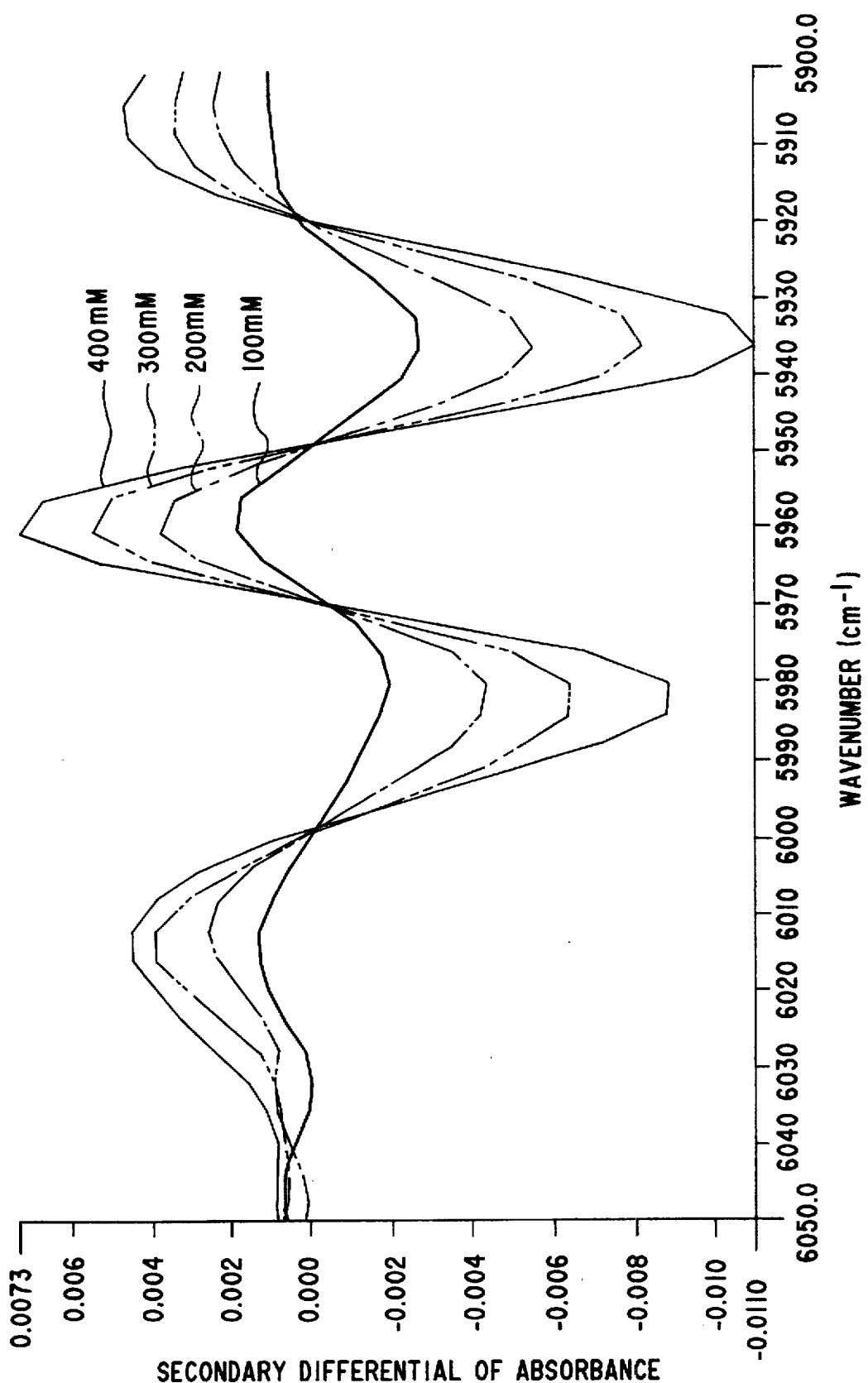
FIG. 5 illustrates results obtained by secondarily differentiating parts of the absorption spectra shown in FIG. 1.

In order to effectively extract a signal which is hard to detect due to influence by an interfering substance, it is effective to perform a multivariate analytical operation after differentiating absorption spectra with respect to wavenumbers or wavelengths. FIG. 4 illustrates results obtained by primarily differentiating parts of the absorption spectra shown in FIG. 1, and FIG. 5 illustrates results obtained by secondarily differentiating parts of the absorption spectra respectively. Also from the results of the primary and secondary differentials, it is clearly understood that spectral intensities are changed in proportion to the concentrations.

Figure 6:
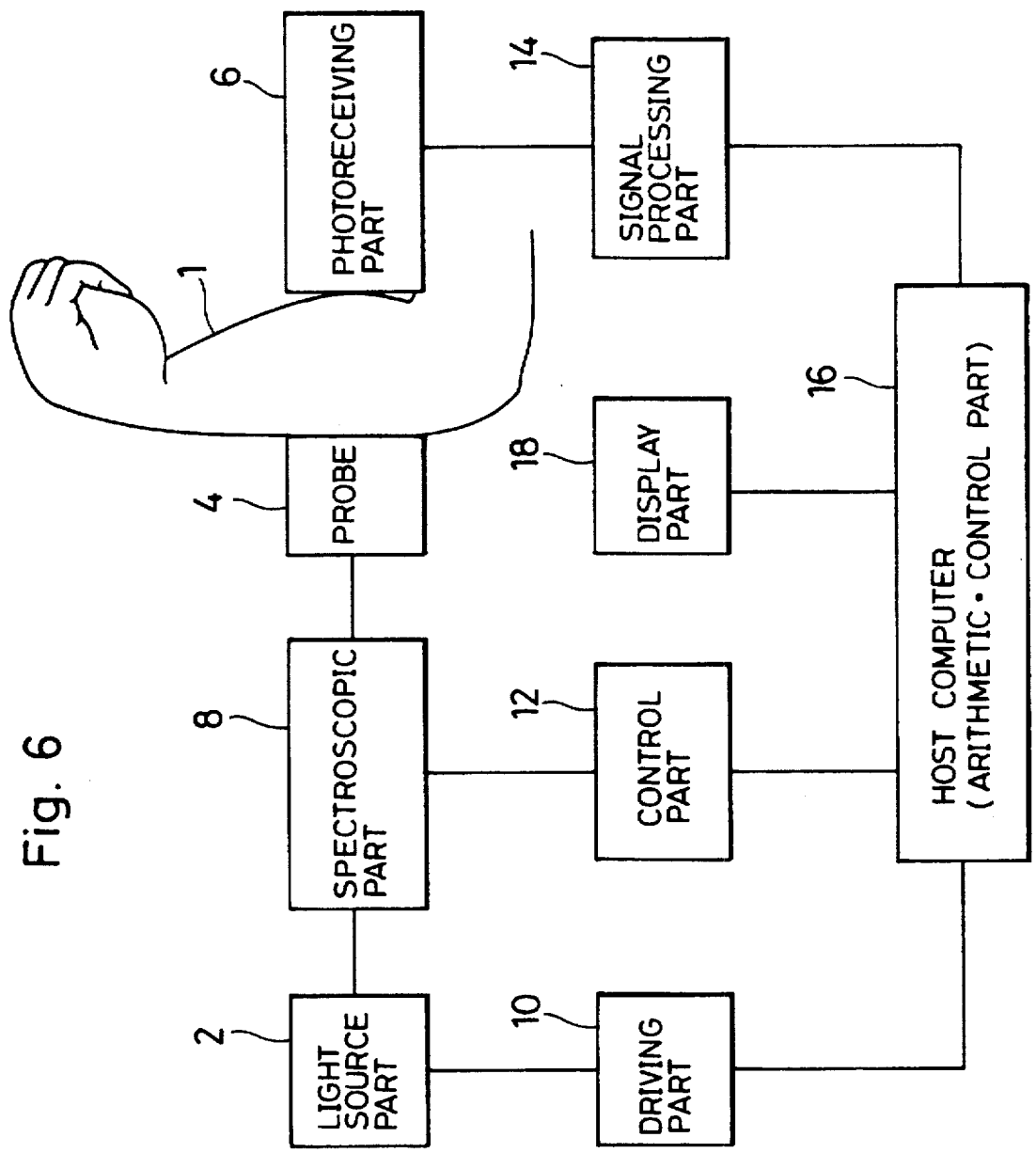
FIG. 6 is a block diagram schematically showing a transmission measuring type embodiment of a lactic acid concentration measuring apparatus.

FIG. 6 schematically illustrates an embodiment of a measuring apparatus for lactic acid in organism according to the present invention. A light source part 2 is formed by a halogen lamp or the like which emits light of a plurality of wavelengths of a near infrared region, and a spectroscopic part 8 is provided on an optical path for irradiating an organism measuring portion 1 with measuring light emitted from the light source part 2 for selecting a wavelength which has an excellent correlation coefficient of at least 0.8 or at least 0.9 between a lactic acid concentration and absorbance in an aqueous lactic acid solution and is selected as a measuring wavelength from the measuring light of a plurality of wavelengths emitted from the light source part 2. A probe 4 comes into contact with the organism measuring portion 1, for irradiating the organism measuring portion 1 with the measuring light of the wavelength selected at the spectroscopic part 8. A photoreceiving part 6 detects transmitted/scattered light of the measuring light which is incident upon the organism measuring portion 1.

The spectroscopic part 8 is of the so-called prespectroscopic system of performing wavelength selection before the organism measuring portion 1 is irradiated with the measuring light, while the spectroscopic part 8 may alternatively be provided on an optical path for introducing the transmitted light of the measuring light into a photodetector element of the photoreceiving part 6 to be of the so-called postspectroscopic system.

Numeral 10 denotes a driving part for driving the light source part 2, numeral 12 denotes a control part for controlling the wavelength selection of the spectroscopic part 8, and numeral 14 denotes a signal processing part for converting a light signal detected by the photoreceiving part 6 to absorbance. Operations of the respective parts are controlled by a host computer 16 serving as an arithmetic-control part, and the concentration of lactic acid is calculated on the basis of a detected transmitted/scattered light intensity. The result of the obtained lactic acid concentration is displayed on a display part 18.

The spectroscopic part 8 may be a monochromatic spectroscope comprising a prism or a diffraction grating, or a Fourier transform spectrophotometer comprising a Michelson interferometer and a Fourier transform arithmetic part in the arithmetic-control part 16. Alternatively, the spectroscopic part 8 may comprise an AOTF (acousto-optical filter), and a high-speed operation is enabled in this case. Further, the spectroscopic part 8 may comprise a plurality of optical filters, for selecting the measuring wavelength by being switched and positioned on the optical path.

The probe 4 is adapted to guide the measuring light to the organism measuring portion 1 by optical fiber, for example. The measuring light is applied from the probe 4, and the light which is transmitted/scattered through/from the organism measuring portion 1 and incident upon the photoreceiving part 6 is strongly scattered by the organism. In order to receive such scattered light, therefore, the photoreceiving part 6 preferably comprises an integrating sphere so that the scattered light collected by the integrating sphere is detected.

The spectroscopic part 8 is necessary when the light source part 2 is formed by a light source such as a lamp emitting light of continuous wavelengths or multiple wavelengths, while the spectroscopic part 8 is unnecessary when the light source part 2 is formed by a laser unit, a laser diode or a light emitting diode emitting single wavelength light. For example, the light source part 2 may comprise a laser diode or a light emitting diode, or a plurality of types of laser diodes or light emitting diodes having different light emitting wavelengths. It is possible to irradiate the organism measuring portion 1 with measuring light of specific wavelengths in a successively switched manner by switching and turning on light emission of these laser diodes or the like. Thus, absorbance measurement with multiple wavelengths can be performed without employing the spectroscopic part 8.

Figure 7:
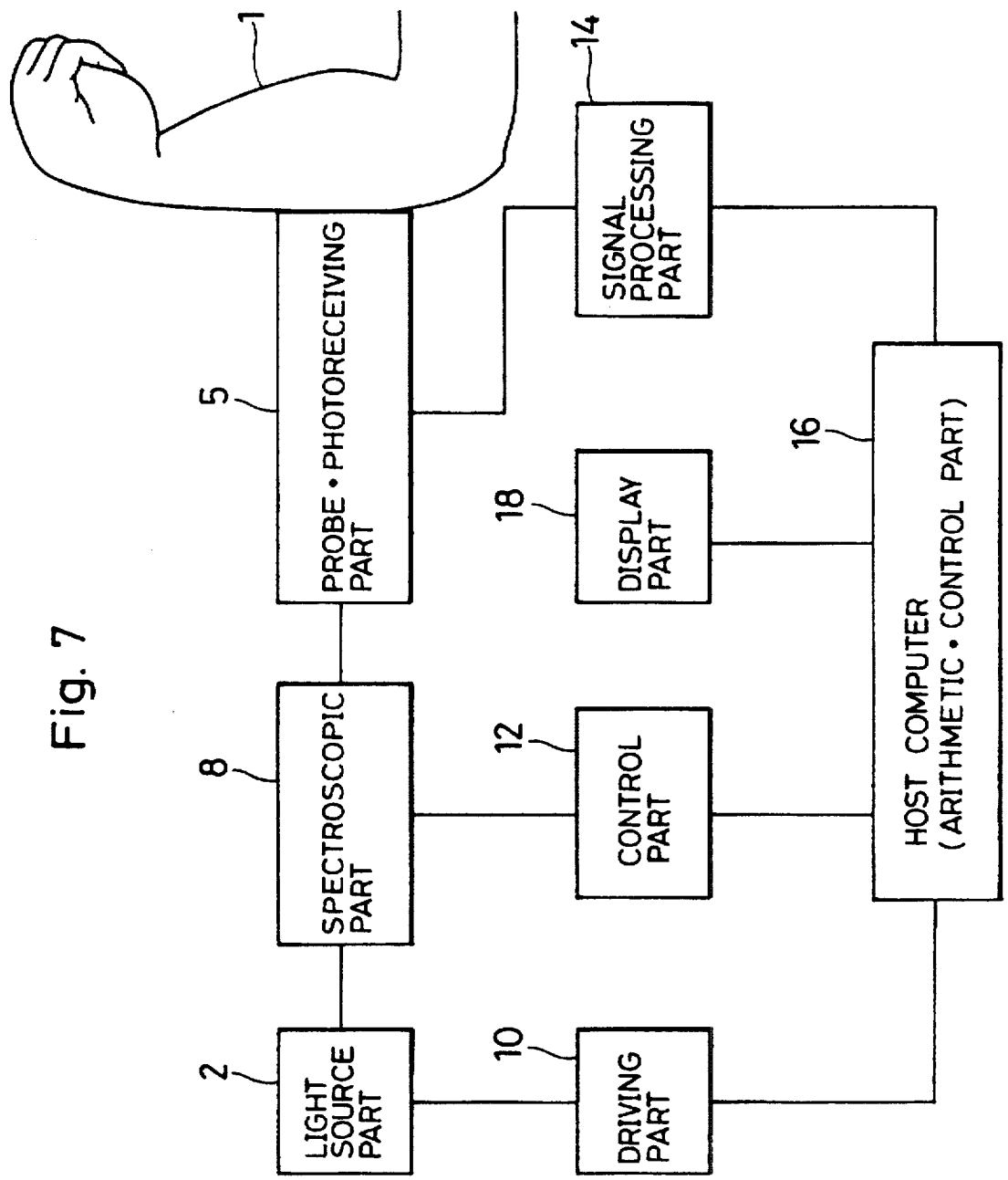
FIG. 7 is a block diagram schematically showing a reflection measuring type embodiment of a lactic acid concentration measuring apparatus.

FIG. 7 shows another embodiment. While the transmitted/ scattered light of the measuring light from the probe 4 is received by the photoreceiving part 6 in the embodiment shown in FIG. 6, a probe and a photoreceiving part are integrated with each other to form a probe-photoreceiving part 5 in the embodiment shown in FIG. 7. Transmitted/ scattered light of measuring light from the probe-photoreceiving part 5 is detected by the probe-photoreceiving part 5. Other structure of this embodiment is identical to that shown in FIG. 6.

FIG. 8 schematically illustrates an embodiment enabling measurement of localized distribution of intravital lactic acid concentrations. A plurality of probe-photoreceiving parts 5-1 to 5-N formed by integrating probes for irradiating an organism 1 with measuring light from a light source and photoreceiving parts for detecting transmitted/scattered light of the measuring light applied from the probes with each other are so provided that the respective probe photoreceiving parts 5-1 to 5-N are in contact with and arranged on different places of the organism 1. The probe-protoreceiving parts 5-1 to 5-N comprise optical fiber, and are adapted to irradiate the organism 1 with the measuring light and receive transmitted/scattered light of the measuring light from the organism 1. Numeral 20 denotes a unit including the light source, a spectroscopic part for selecting measuring light of a prescribed measuring wavelength from the light emitted from the light source and transmitting the same to the probe-protoreceiving parts 5-1 to 5-N, a photoreceiving part for detecting the transmitted/scattered light from the organism 1 received by the probe-photoreceiving parts 5-1 to 5-N, and a data processing part for performing prescribed data processing of converting a light signal detected by the photoreceiving part to absorbance etc. The respective places of the organism 1 on which the probe-protoreceiving parts 5-1 to 5-N are arranged and lactic acid concentrations are associated with each other by a host computer 16 of an arithmetic-control part, and displayed on a display part 18 as images.

The photoreceiving part included in the unit 20 is a multichannel photoreceiving part simultaneously detecting the transmitted/scattered light from the organism 1 received by the probe-photoreceiving parts 5-1 to 5-N, and can measure localized distribution of the lactic acid concentrations in the organism 1 in a short time.

In the embodiment shown in FIG. 8, only a set of the probe-photoreceiving part may be provided. In this case, the probe-photoreceiving part is movably supported to be capable of scanning different places of the organism 1, while a memory device is necessary for temporarily storing a light signal received in each part with information of the places. Localized distribution of the lactic acid concentrations is obtained from the light signal stored in the memory device, so that the result is displayed on the display part 18.

FIG. 9A schematically illustrates an embodiment which can obtain a tomographic image of an organism I by a lactic acid concentration. FIG. 9B illustrates the structure of a portion around the organism 1. A probe-photoreceiving part 5 is supported by a support member 30 on a circumference enclosing the organism 1. The support member 30 supports the probe-photoreceiving part 5 to be slidable in the direction of the organism 1 so that the forward end surface of the probe-photoreceiving part 5 comes into contact with the organism 1, and to be capable of moving along the periphery of the organism 1 and scanning the same. A unit 22 comprises a light source, a spectroscopic part for selecting measuring light of a prescribed measuring wavelength from light generated from the light source and transmitting the same to the probe-photoreceiving part 5, and a photoreceiving part for detecting transmitted/scattered light from the organism 1 received by the probe-photoreceiving part 5. Numeral 24 denotes a data processing-driving part for driving scanning of the probe-photoreceiving part 5 by the support member 30 to move along the periphery of the organism 1.

A tomographic image of the organism 1 by the lactic acid concentration is reconstructed by a host computer 16 of an arithmetic-control part from data obtained by the probe-photoreceiving part 5 moving around the organism 1, to be displayed on a display unit 28 through a concentration distribution display part 26.

It is possible to obtain a tomographic image of another place of the organism 1 by moving the support member 30 as shown by arrow in FIG. 9B.

As a modification of the embodiment shown in FIGS. 9A and 9B, a single probe for applying measuring light and a multichannel photoreceiving part having a plurality of photoreceiving elements can be arranged on the support member 30 to enclose the organism 1. Transmitted/scattered light of measuring light which is introduced into the organism 1 from the probe is simultaneously detected by the multichannel photoreceiving part around the organism 1. It is possible to reconstruct a tomographic image of the organism 1 by the lactic acid concentration through data obtained by rotating the probe and the multichannel photoreceiving part around the organism 1 by the support member 30.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A measuring apparatus for lactic acid concentration in an organism comprising: a light source part emitting an input light having a wavelength in a near infrared region wherein said wavelength is a wavelength whose correlation coefficient between said lactic acid concentration and absorbance is at least 0.8 in aqueous lactic acid solution measurement;

a probe for coming into contact with a tissue measuring portion for irradiating said tissue measuring portion with said input light from said light source part;

a photoreceiving part for detecting an intensity of an output light being received from said tissue measuring portion; and an arithmetic part for calculating a lactic acid concentration on the basis of said intensity of said out put light at one or a plurality of measuring wavelengths, detected by said photoreceiving part, being subjected to absorption.

2. The measuring method in accordance with claim 1, wherein said measuring wavelength is selected from near infrared regions being expressed in wavenumbers of 6300 to 5400 $cm^{-1}$ and 4800 to 4200 $cm^{-1}$.

3. The measuring apparatus in accordance with claim 1, wherein said light source part emits light of a plurality of wavelengths of said near infrared region, said apparatus further comprising a spectroscopic part being provided on an optical path for irradiating said organism measuring portion with said measuring light or an optical path for introducing said transmitted/scattered light of said measuring light into said photoreceiving part for selecting one or a plurality of wavelengths being subjected to absorption by lactic acid as said measuring wavelength(s) from said light of said plurality of wavelengths being emitted from said light source part.

4. The measuring apparatus in accordance with claim 1, wherein said light source part comprises any of a laser unit, a laser diode and a light emitting diode emitting light of said wavelength(s) of said near infrared region being said wavelength(s) subjected to absorption by lactic acid and selected as said measuring wavelength(s).

5. The measuring apparatus in accordance with claim 4, wherein said light source part includes a plurality of types of laser diodes or light emitting diodes having different emission wavelengths for successively generating said measuring light of a plurality of wavelengths by being successively switched and turned on.

6. The measuring apparatus in accordance with claim 1, wherein said probe consists of a plurality of probes being arranged on different tissue measuring portions respectively for simultaneously irradiating said plurality of measuring portions with said light, and said photoreceiving part comprises a multichannel photoreceiving part which has a plurality of photoreceiving elements being arranged on respective positions corresponding to respective said probes for simultaneously detecting said output light resulting from said input light being applied from respective said probes, said apparatus further comprising a display part for imaging and displaying lactic acid concentrations of respective said measuring portions being calculated by said arithmetic part in correspondence to said measuring portions.

7. The measuring apparatus in accordance with claim 1, wherein a set of said probe and said photoreceiving part corresponding thereto are provided, and said probe and said photoreceiving part are supported to be capable of scanning different measuring portions of said organism in a state keeping mutual positional relation therebetween, said apparatus further comprising:

a memory device for storing lactic acid concentrations of respective said measuring portions being calculated by said arithmetic part in correspondence to said measuring portions, and a display part for imaging and displaying lactic acid concentration distribution on the basis of data being stored in said memory device.

8. The measuring apparatus in accordance with claim 1, wherein one said probe and said photoreceiving part are arranged on a circumference enclosing said organism, said photoreceiving part is a multichannel photoreceiving part simultaneously detecting transmitted and scattered output light of said measuring light of said measuring light being applied from said probe being applied from said probe, and said probe and said photoreceiving part are supported to rotatively move along said circumference, said apparatus further comprising:

an image processor for forming a tomographic image by said intravital lactic acid concentration on the basis of lactic acid data of respective measuring portions being calculated by said arithmetic part on the basis of light signals being detected by said photoreceiving part, and a display part for displaying said tomographic image.

9. A measuring apparatus for measuring the concentration of lactic acid in an organism as in claim 1 wherein said output light is the input light which has been transmitted through said organism.

10. A measuring apparatus for measuring the concentration of lactic acid in an organism as in claim 1 wherein said output light is the input light which has been scattered from said organism.

11. A measuring method for quantitatively analyzing an intravital lactic acid concentration in an organism comprising the steps of:

irradiating said organism with an input light having a near infrared measuring wavelength whose correlation coefficient between said lactic acid concentration and absorbance is at least 0.8 in aqueous lactic acid solution measurement;

detecting an intensity of an output light at said measuring wavelength emitting from said organism; and determining a concentration of said intravital lactic acid quantitatively on the basis of said output light intensity.

12. The measuring method in accordance with claim 11, wherein light intensities at measuring wavelengths are detected from said light being emitted from said organism respectively on the assumption that a plurality of wavelengths being subjected to absorption by lactic acid in a near infrared region are said measuring wavelengths, so that said intravital lactic acid concentration is quantitatively analyzed from said light intensities with multivariate analysis.

13. The measuring method in accordance with claim 12 wherein said measuring wavelengths are selected from near infrared regions being expressed in wavenumbers of 6300 to 5400 $cm^{-1}$ and 4800 to 4200 $cm^{-1}$.

14. A measuring method for quantitatively analyzing an intravital lactic acid concentration in an organism as in claim 11 wherein said output light is the input light which has been transmitted through said organism.

15. A measuring method for quantitatively analyzing an intravital lactic acid concentration in an organism as in claim 11 wherein said output light is the input light which has been scattered from said organism.

16. The measuring method in accordance with claim 12, wherein said measuring wavelength is from 6300 to 5400 $cm^{-1}$.

17. The measuring method in accordance with claim 12, wherein said measuring wavelength is from 4800 to 4200 $cm^{-1}$.

* * * * *